(12) United States Patent
Lartey et al.

(10) Patent No.: US 9,974,441 B2
(45) Date of Patent: May 22, 2018

(54) FEVER DETECTOR WRIST BAND

(71) Applicants: Seth O. Lartey, Winston-Salem, NC (US); Jacqueline Williams Lartey, Winston-Salem, NC (US)

(72) Inventors: Seth O. Lartey, Winston-Salem, NC (US); Jacqueline Williams Lartey, Winston-Salem, NC (US)

( * ) Notice: Subject to any disclaimer, the term of this patent is extended or adjusted under 35 U.S.C. 154(b) by 155 days.

(21) Appl. No.: 14/820,383

(22) Filed: Aug. 6, 2015

(65) Prior Publication Data

US 2016/0367149 A1  Dec. 22, 2016

Related U.S. Application Data

(60) Provisional application No. 62/181,211, filed on Jun. 18, 2015.

(51) Int. Cl.
*A61B 5/01*  (2006.01)
*A61B 5/00*  (2006.01)
(Continued)

(52) U.S. Cl.
CPC ............ *A61B 5/01* (2013.01); *A61B 5/681* (2013.01); *A61B 5/6824* (2013.01);
(Continued)

(58) Field of Classification Search
CPC ....................................................... A61B 5/01
(Continued)

(56) References Cited

U.S. PATENT DOCUMENTS 242,605 A * 6/1881 Van Kersen ............. A24C 3/00
 131/32
252,136 A * 1/1882 Khemka ................ A01D 46/02
 460/126
(Continued)

FOREIGN PATENT DOCUMENTS

KR  20110002553 U  *  3/2011

OTHER PUBLICATIONS

Vacu Vin Snap Thermometer, which was publicly available on Jun. 28, 2013 on You Tube: https://www.youtube.com/watch?v=yZh2aiMWZwM.*

*Primary Examiner* — Jason C Olson
(74) *Attorney, Agent, or Firm* — Everman Law Firm, P.A.; Gregory R. Everman

(57) ABSTRACT

A fever detecting wrist band device comprises a flexible band and a fever detection device attached to the flexible band. The fever detection device comprises a thermochromic liquid crystal (TLC) material, which can change colors corresponding to a set of temperature ranges, encased in a transparent casing. The transparent casing has a thin bottom section to allow the TLC material to gather body heat when the wrist band is worn by a user and the bottom section comes in contact with the skin of the user. The transparent casing also insulates the TLC material from all sides which are not in contact with the skin of the user so that surrounding temperature of a user does not affect the color change of the TLC material. When the user wears the fever detecting wrist band device, the TLC material might change color indicating a higher body temperature of the user which in turn could indicate that either the user has a fever or the user might have a fever soon if not treated immediately.

3 Claims, 2 Drawing Sheets

(51) Int. Cl.
*G01K 11/16* (2006.01)
*G01K 13/00* (2006.01)
(52) U.S. Cl.
CPC ............ *A61B 5/6831* (2013.01); *A61B 5/742* (2013.01); *G01K 11/165* (2013.01); *G01K 13/002* (2013.01); *A61B 2562/0276* (2013.01)
(58) Field of Classification Search
USPC ........................................................ 600/549
See application file for complete search history.

(56) References Cited

U.S. PATENT DOCUMENTS

| | | | | |
|---|---|---|---|---|
| 281,147 | A | * | 7/1883 | Khemka ................ A43D 3/026 12/137 |
| 317,129 | A | * | 5/1885 | Beranek et al. .......... D01F 9/16 427/227 |
| 414,435 | A | * | 11/1889 | Nahon ................... B60G 11/08 278/81 |
| 4,509,531 | A | * | 4/1985 | Ward ....................... A61B 5/01 374/142 |
| 6,238,354 | B1 | * | 5/2001 | Alvarez ................. G01K 1/024 374/100 |
| 2013/0119255 | A1 | * | 5/2013 | Dickinson .............. G04G 21/00 250/340 |

\* cited by examiner

FEVER DETECTOR WRIST BAND

FIELD OF THE INVENTION

The present invention relates generally to non-invasive systems to determine physiological conditions of a person. The present invention is more particularly directed to a wrist band with fever detection capabilities.

BACKGROUND OF THE INVENTION

As the world becomes increasingly connected and mobile, people travel frequently from one part of the world to another. In the process they might carry germs of communicable diseases with them affecting other people who come in their contact. With recent outbreaks of epidemics like Ebola, which caused a wide-spread panic with strict travel restrictions to and from countries identified as high risk by WHO for communicable diseases, such as Guinea and Sierra Leone, it becomes increasingly necessary to identify people who may have been affected with a communicable disease requiring immediate attention or could be on the verge of falling sick. Usually a simple yet reliable indicator of many communicable diseases is fever. However, it often goes unnoticed till the body temperature gets really high indicating significant spread of disease. If this change in temperature can be identified quickly, preferably at the onset, it ma help in faster response in terms of initiating countermeasures which in turn may result in faster recovery of the patient as well as more effective containment of the spread of the disease.

Similar requirement exists in the 'high risk' countries, many of these on the African continent, where not just the local population but people involved in the relief efforts are also always at high risk due to being in constant contact with potential patients. What complicates the problem further is lack of power sources which makes it extremely difficult to use sophisticated machines for detection, especially in rural areas where most of the potentially affected population lives. Even using battery-operated portable devices often prove difficult due to the need of frequent replacements. In many areas even procuring new batteries may prove difficult.

Apart from the issue of power, another issue which makes operating these systems difficult in these areas is the storage (protection from rain, sunlight, etc.) and regular maintenance requirements as procuring new parts and availing qualified repair services is again difficult and costly. Even storing and travelling with simple, mercury-based glass thermometers may prove difficult for the relief personnel as these are quite susceptible to shocks and can easily break releasing toxic mercury which in turn can pose health hazards.

Clearly, there is a requirement for a device which is low-maintenance, durable, doesn't need power to operate, can be used with minimal training and should be easy to carry around and store. Such as device should be useful to the relief personnel to keep an eye on their temperature while working in the affected areas and should allow them to use the same device with potential patients, as a backup to the existing devices being used in the field. The present invention provides such a device with the aforementioned features.

All the advantages and features of the present invention will be set forth in the description which follows, and will become apparent to those skilled in the art upon examination of the following, or may be learned by practice of the invention. These advantages and features of the present invention will be more readily apparent when considered in reference to the following description and when taken in conjunction with the drawings below.

DETAILED DESCRIPTION OF THE INVENTION

Figure 1:
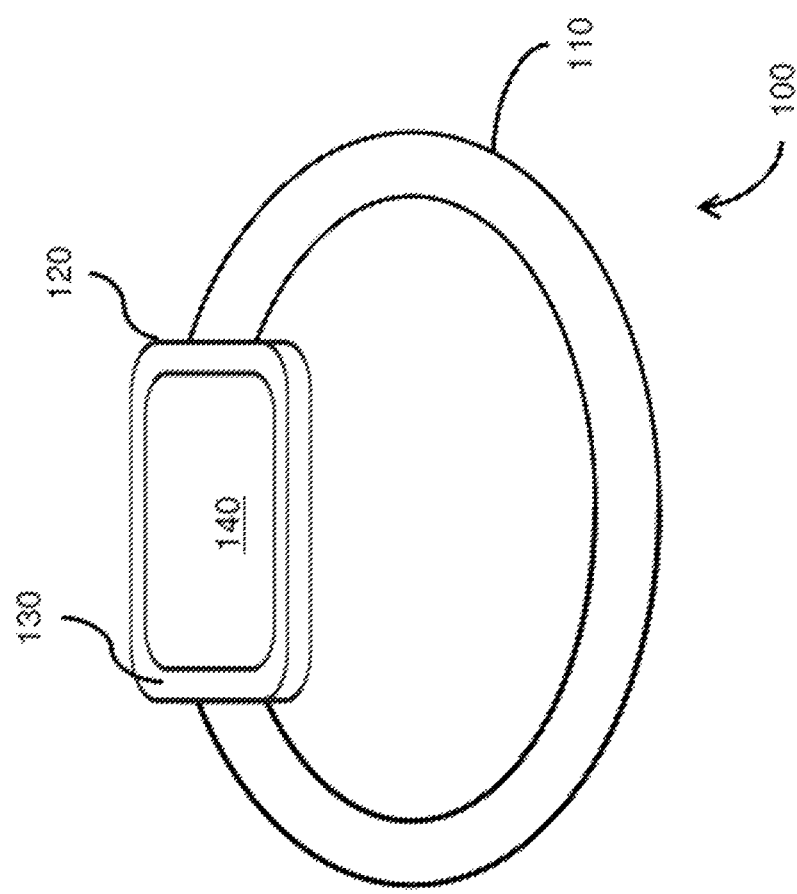
FIG. 1 is a top perspective view of a fever detecting wrist band device as per an exemplary non-limiting embodiment of the present invention.
Figure 2:
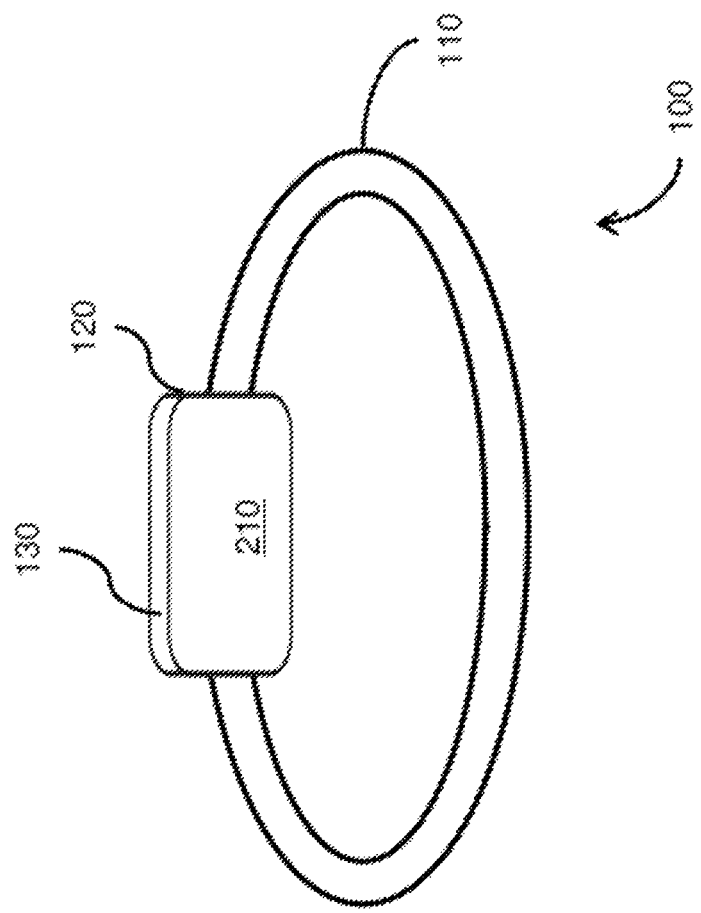
FIG. 2 is a bottom perspective view of a fever detecting wrist band device as per the exemplary non-limiting embodiment of the present invention.

Construction and working of a fever detecting wrist band device as per the present invention has been explained henceforth using exemplary non-limiting embodiments of the present invention with reference to FIGS. 1 and 2.

As per an exemplary non-limiting embodiment of the present invention, the fever detecting wrist band device 100 comprises a band 110 made of a flexible material or compound, such as silicone rubber, which can regain its shape despite getting stretched multiple times for prolonged periods of time. The wrist band 110 helps a user to wear the fever detecting wrist band 100 on either of the wrists of the user. It will be apparent to those skilled in the art that several materials and compounds known in the existing art, having desired properties, can be used for the wrist band 110. In an embodiment of the present invention, the wrist band 110 may have an outer cover of flexible or semi-rigid material durable and strong enough to withstand climatic conditions as well as wear or tear due to daily use, sweat, etc.

The fever detecting wrist band device 100 also comprises a fever detection device 120 attached to the wrist band 110. The fever detection device 120 comprises a thermochromic liquid crystal (TLC) material, such as cholesteric liquid crystals or ferroelectric liquid crystals, which can change color from a color A to a color B, through a series of colors in between, and vice-versa in response to a change in temperature. For example, at a room temperature X a TLC material may have a green color which slowly changes to a yellow color as temperature increases, and finally turns red when the temperature crosses a threshold temperature Y. It will be apparent to those skilled in the art that several TLC materials known in the existing art, having desired properties, can be used in the fever detection device. Further, the initial time taken by a TLC material to change color corresponding to an initial change in temperature may depend on the specific properties of the TLC material which can be tabulated from observation and used as an initial pre-defined time threshold references.

The fever detection device 120 also comprises a casing 130 with a transparent top surface 140 to encase the TLC material. The casing 130 should preferably be thin at a bottom section 210 of the fever detection device 120 to allow the encased TLC material to gather body heat when the bottom section 210 is put in contact with skin of a person. In an embodiment of the present invention, this thin bottom section 210 can be protected by a partially removable insulating cover, using various means known in the existing art, so that the thin bottom section 210 can be exposed to the skin of the person only when required. In another embodiment of the present invention, the entire casing 130 might be removed. The casing 130 preferably should also insulate the fever detection device 120 from all the sides which are not in contact with the skin of the person else the ambient temperature fluctuations might cause a change in color of the TLC material, in case the person is working in a very hot environment, such as that of the African continent, and this might give a false positive identification of the user running a fever. In another embodiment of the present invention, the casing 130 will insulate the fever detection device 120 from all sides, when not in use, to ensure the ambient temperature fluctuations do not cause a change in color of the TLC material, in case the person is working in a very hot environment, such as that of the African continent.

The following section explains a preferred method of use of the fever detecting wrist band device 100. When a user wears the fever detecting wrist band device 100, the bottom section 210 of the fever detection device 120 comes in contact with the skin of the user which allows the encased TLC material to gather body heat of the user. Once an initial pre-defined time threshold has passed, depending on the TLC material used, the TLC material will either change color to one of the pre-determined colors corresponding to one of the temperature ranges, as per the TLC material properties, or will remain in the same color. If the TLC material doesn't change color, it would indicate that the user does not have fever at the moment. However, if the TLC material changes color it would indicate that either he has a fever or he is about to have fever as the body temperature is close to the fever temperature. Now as the user wears the fever detecting wrist band device 100 regularly, while working or otherwise, the color of the TLC material might change at any point of time in case the body temperature of the user increases indicating the user has or is about to have fever.

A non-limiting example of the above can be a fever detecting wrist band device 100, where a TLC material used can have one of these three colors:

1) Green: this is the color of the TLC material at or below body temperature of a user
2) Yellow: this is the color of the TLC material when the body temperature of the user is in a temperature range close to a pre-determined cut-off temperature indicating fever
3) Red: this is the color of the TLC material when the body temperature of the user is at or above the pre-determined cut-off temperature indicating fever Now, when the user wears the non-limiting exemplary fever detecting wrist band device 100, then after an initial pre-defined time threshold the TLC material would stabilize in terms of colors and would have one of the three colors, Green, Yellow or Red indicating the corresponding state of the body temperature. Even later, during the regular use of the fever detecting wrist band device 100, if the body temperature of the user changes the color of the TLC material would in turn result in a change of color indicating onset of or having fever. This will quickly give an indication to the user to seek medical help at the earliest.

The user might also use the fever detecting wrist band device 100 to quickly check if a person other than the user has fever or not, by twisting the wrist band 110 inside out, such that the inner surface of the wrist band 110 would become the outer surface and the bottom section 210 of the fever detection device 120 would come to the top, and keeping the bottom section 210 in contact with the forehead of the person for an initial pre-defined time threshold to allow for any possible color change.

Various modifications to the above described invention will be readily apparent to those skilled in the art and the general principles defined herein may be applied to other embodiments and applications without departing from the spirit and scope of the present invention. Thus, the present invention is not intended to be limited to the embodiments described, but is to be accorded the widest scope consistent with the principles and features disclosed herein. Therefore, the scope of the invention is to be determined by the terminology of the above description and the legal equivalents thereof.

What is claimed is:

1. A fever detection device comprising:
   a thermochromic liquid crystal material;
   a casing encasing the thermochromic liquid crystal material and having a bottom section capable of allowing heat transfer from a user to the thermochromic liquid crystal material when the bottom section is in contact with the skin of the user;
   a cover, wherein the cover may selectively be positioned in a protective position wherein the cover insulates the bottom section from heat transfer from the user and an exposed position wherein the bottom section is exposed such that the bottom section is capable of being placed in contact with the skin of the user;
   an attachment device, wherein the attachment device comprises a wristband that allows for the fever detection device to be removably attached to the user; and
   wherein the thermochromic liquid crystal material changes color to a predetermined color in response to a body temperature of the user.

2. The fever detection device of claim 1, wherein the wristband comprises a flexible material.

3. The fever detection device of claim 1, wherein the wristband comprises an outer cover of a material durable enough to withstand climatic conditions, bodily fluids of the user, and wear and tear due to daily use by the user.

* * * * *